(12) United States Patent
Nagaike

(10) Patent No.: US 8,531,664 B2
(45) Date of Patent: Sep. 10, 2013

(54) PARTICLE NUMBER MEASUREMENT METHOD

(75) Inventor: Hiroshi Nagaike, Yamanashi (JP)

(73) Assignee: Tokyo Electron Limited, Tokyo (JP)

(*) Notice: Subject to any disclaimer, the term of this patent is extended or adjusted under 35 U.S.C. 154(b) by 265 days.

(21) Appl. No.: 13/036,152

(22) Filed: Feb. 28, 2011

(65) Prior Publication Data

US 2011/0216318 A1  Sep. 8, 2011

Related U.S. Application Data

(60) Provisional application No. 61/321,295, filed on Apr. 6, 2010.

(30) Foreign Application Priority Data

Mar. 2, 2010 (JP) ................................. 2010-045414

(51) Int. Cl.
*G01N 21/00* (2006.01)
(52) U.S. Cl.
USPC .......................................... 356/338; 356/341
(58) Field of Classification Search
USPC . 356/335–343; 73/23.2–23.24, 28.01–28.06, 73/31.05, 31.07, 31.01; 250/216, 573–577
See application file for complete search history.

(56) References Cited

U.S. PATENT DOCUMENTS

| 6,661,514 B1 * | 12/2003 | Tevs et al. ...................... 356/337 |
| 7,458,247 B2 * | 12/2008 | Moriya et al. ................ 73/28.01 |
| 2008/0041723 A1 | 2/2008 | Manaresi et al. |

FOREIGN PATENT DOCUMENTS

| CN | 101076717 A | 11/2007 |
| JP | 11-330053 A | 11/1999 |
| JP | 2000-155086 A | 6/2000 |
| JP | 2005-317900 A | 11/2005 |

* cited by examiner

*Primary Examiner* — Tri T Ton
(74) *Attorney, Agent, or Firm* — Pearne & Gordon LLP

(57) ABSTRACT

There is provided a particle number measurement method capable of accurately measuring the number of particles generated by a specific factor. When the number of particles is measured by irradiating laser beam 25 into a main exhaust line 16 via a glass window 24, receiving lights (L1 and L2) scattered from particles (P1 and P2) crossing with the laser beam 25 by a photodetector 21, and calculating the number of particles based on the received scattered light, static particles P2 are considered as contaminants attached to the glass window 24 and the number of static particles P2 is subtracted from the measured number of particles within the main exhaust line 16.

5 Claims, 8 Drawing Sheets

DETECTED POSITION OF PARTICLE
(OSILLATION ANGLE OF LASER BEAM)

*FIG. 7A*  *FIG. 7B*
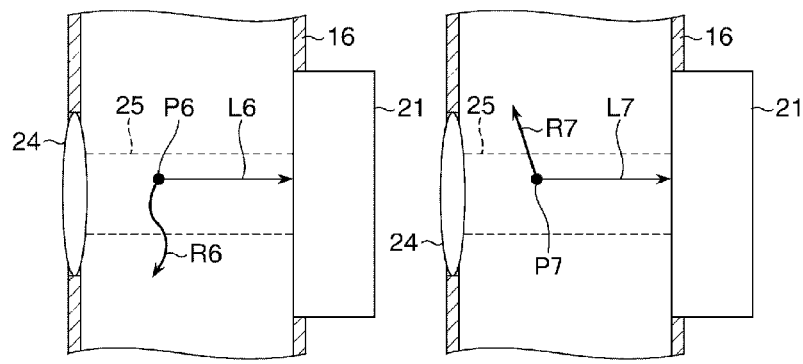
*FIG. 7C*
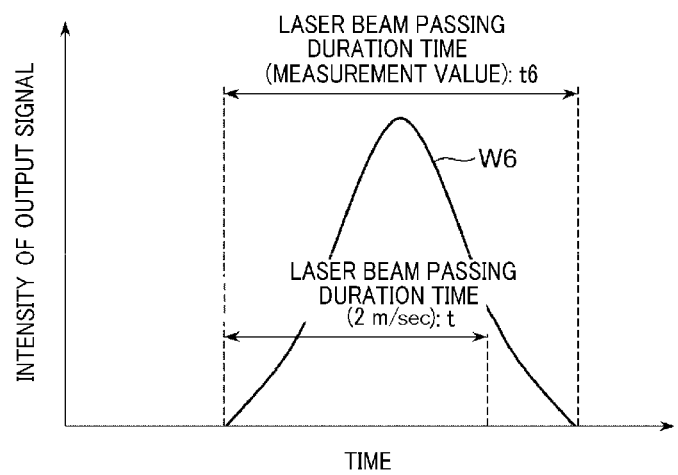

PARTICLE NUMBER MEASUREMENT METHOD

CROSS-REFERENCE TO RELATED APPLICATION

This application claims the benefit of Japanese Patent Application No. 2010-045414 filed on Mar. 2, 2010 and U.S. Provisional Application Ser. No. 61/321,295 filed on Apr. 6, 2010, the entire disclosures of which are incorporated herein by reference.

FIELD OF THE INVENTION

The present disclosure relates to a particle number measurement method; and, more particularly, to a particle number measurement method for measuring the number of particles by receiving light scattered from a particle to which laser beam is irradiated.

BACKGROUND OF THE INVENTION

In a conventional substrate processing apparatus for processing a wafer, the number of particles moving within a processing chamber or a gas exhaust line is measured in order to check a state within the processing chamber or the gas exhaust line. Generally, an ISPM (In Situ Particle Monitor) is used to measure the number of particles. The ISPM may include a laser beam oscillator for irradiating laser beam into the processing chamber or the gas exhaust line; and a photodetector for receiving light scattered from a particle passing through the laser beam (hereinafter, referred to as "particle-scattered light"). The ISPM converts the received scattered light to an electrical signal and measures the number of particles based on the magnitude of the electrical signal.

Meanwhile, in the substrate processing apparatus for processing a wafer by plasma, the plasma is generated in the processing chamber, so that the photodetector receives light emitted from plasma in addition to the particle-scattered light. Accordingly, the light from plasma may be mistakenly detected as the particle-scattered light, which makes it difficult to accurately measure the number of particles.

For this reason, there has been recently developed a particle monitoring method capable of preventing decrease in sensitivity of monitoring particle by calculating a brightness difference between an image acquired by monitoring the inside of a processing chamber and a reference background image corresponding to an operation state of a substrate processing apparatus (see, e.g., Patent Document 1) or a method for monitoring a contamination status within a processing chamber in real time by distinguishing particle-scattered light from light emitted from plasma by separating scattered light into predetermined wavelength components and extracting desired frequency components therefrom (see, e.g., Patent Document 2).

Meanwhile, a high intensity scattered light may be generated from a relatively large foreign substance (particle) attached to a window of a photomultiplier tube or a window of a laser beam oscillator through which laser or scattered light passes, or a relatively high intensity scattered light such as cosmic rays may enter the processing chamber from the outside. In this case, there may be used a method for excluding influence of the relatively high intensity scattered light from the particle number measurement by removing the scattered light having intensity higher than a predetermined level from the received scattered light.

Meanwhile, along with miniaturization of semiconductor devices manufactured from a wafer, a particle size that affects the performance of the semiconductor devices is reduced to several tens of nanometers. Therefore, the number of particles having a size of several tens of nanometers needs to be measured accurately.

Moreover, in order to more accurately check a state within the processing chamber or the gas exhaust line, it is required to accurately measure the number of particles generated by a specific factor among a multiple number of scattering particles.

However, particles having a size of several tens of nanometers may be generated by another factor different from the specific factor. Besides, the particles having a size of several tens of nanometers may be attached to a window of a laser beam oscillator or a window of a photomultiplier tube. That is, the measured number of particles having a size of several tens of nanometers may include the number of particles generated by the specific factor and the number of particles generated by another factor different from the specific factor. Hence, the number of particles generated by another factor different from the specific factor needs to be subtracted from the measured number of particles having a size of several tens of nanometers.

Patent Document 1: Japanese Patent Laid-open Publication No. 2000-155086

Patent Document 1: Japanese Patent Laid-open Publication No. H11-330053

However, in the above-described conventional methods, the scattered light is distinguished based on the intensity thereof, i.e., the size of particles, so that it is difficult to accurately measure the number of particles generated by a specific factor among a multiple number of same-sized particles generated by different factors.

BRIEF SUMMARY OF THE INVENTION

In view of the above, the present disclosure provides a particle number measurement method capable of measuring the number of particles generated by a specific factor.

In accordance with one aspect of the present disclosure, there is provided a particle number measurement method including measuring the number of particles generated by a specific factor and moving within a predetermined space. Here, the number of particles moving within the predetermined space at a moving speed lower than a predetermined moving speed or moving in a direction opposite to a predetermined moving direction is subtracted from the measured number of particles.

In the particle number measurement method, the number of particles may be measured by irradiating laser beam into the predetermined space via a window, receiving light scattered from a particle crossing with the laser beam, and calculating the number of particles based on the received scattered light. Static particles within the predetermined space may be considered as contaminants attached to the window and the number of static particles may be subtracted from the measured number of particles.

In the particle number measurement method, the specific factor may include a process of removing particles within a processing chamber of a substrate processing apparatus by purging the processing chamber by a gas at a high flow rate.

In the particle number measurement method, the predetermined space may be the inside of the processing chamber, the inside of the processing chamber may be exhausted to a vacuum state, and the predetermined moving speed may be about 1 m/sec.

In the particle number measurement method, the predetermined space may be the inside of a gas exhaust line for exhausting gas from the inside of the processing chamber, the inside of the processing chamber may be exhausted to a vacuum state, and the predetermined moving speed may be about 2 m/sec.

In the particle number measurement method, the predetermined space may be the inside of a gas exhaust line for exhausting gas from the inside of the processing chamber, the inside of the processing chamber may be exhausted to a vacuum state, and the predetermined moving direction may be a direction in which the gas flows in the gas exhaust line.

In accordance with the particle number measurement method, the number of particles moving within the predetermined space at a moving speed lower than a predetermined moving speed or moving in a direction opposite to a predetermined moving direction is subtracted from the measured number of particles. The same-sized particles generated by different factors may have different moving speeds. Accordingly, the number of particles moving within the predetermined space at a moving speed lower than a predetermined moving speed or moving in a direction opposite to a predetermined moving direction is subtracted from the measured number of particles, and, thus, the number of particles generated by the specific factor can be accurately measured.

In accordance with the particle number measurement method, the static particles within the predetermined space are subtracted from the measured number of particles. The static particles as contaminants attached to the window may not be moved. Accordingly, the number of the static particles within the predetermined space is subtracted from the measured number of particles, the number of the particles attached to the window as contaminants can be accurately excluded.

In accordance with the particle number measurement method, the specific factor includes the process of removing particles within the processing chamber of a substrate processing apparatus by purging the processing chamber by a gas at a high flow rate. The particles generated by the process of removing particles may be moved at a high speed by a high speed gas flow created by the purge gas at a high flow rate. Accordingly, the number of particles having a moving speed of lower than a predetermined moving speed within the predetermined space is subtracted from the measured number of particles, and, thus, the number of particles generated by the process of removing particles can be accurately measured.

In accordance with the particle number measurement method, the predetermined space is the inside of the processing chamber, the inside of the processing chamber is exhausted to a vacuum state, and the predetermined moving speed is about 1 m/sec. The particles generated by the process of removing particles are moved at a speed of about 1 m/sec or higher within the processing chamber by a high speed gas flow created by the purge gas at a high flow rate. Accordingly, the number of particles having a moving speed of lower than about 1 m/sec is subtracted from the measured number of particles, and, thus, the number of particles generated by the process of removing particles within the processing chamber can be accurately measured.

In accordance with the particle number measurement method, the predetermined space is the inside of a gas exhaust line for exhausting gas from the inside of the processing chamber, the inside of the processing chamber is exhausted to a vacuum state, and the predetermined moving speed is about 2 m/sec. The particles generated by the process of removing particles are moved at a speed of about 2 m/sec or higher within the exhaust line by a high speed gas flow created by the purge gas at a high flow rate. Accordingly, the number of particles having a moving speed lower than about 2 m/sec is subtracted from the measured number of particles, and, thus, the number of particles generated by the process of removing particles can be accurately measured within the exhaust line.

In accordance with the particle number measurement method, the predetermined space is the inside of a gas exhaust line for exhausting gas from the inside of the processing chamber, the inside of the processing chamber is exhausted to a vacuum state, and the predetermined moving direction is a direction in which the gas flows in the gas exhaust line. The particles may be returned into the exhaust line by a rotator wing rotating at a high speed within a pump on a downstream of the exhaust line and moved in a direction opposite to the direction in which the gas flows in the exhaust line. Accordingly, the number of particles moving in a direction opposite to the direction in which the gas flows, i.e., the number of particles returned from the pump, is subtracted from the measured number of particles, and, thus, the number of particles generated by the process of removing particles can be accurately measured within the exhaust line.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore, not to be intended to limit its scope, the disclosure will be described with specificity and detail through use of the accompanying drawings, in which:

FIG. 2A is a horizontal cross sectional view of the ISPM and FIG. 2B is a graph showing distribution of the number of particles measured by the ISPM;

FIG. 3A is a horizontal cross sectional view of the ISPM, FIG. 3B is a front view of a linear anode PMT of a photodetector used in the ISPM, and FIG. 3C is a graph showing distribution of the number of particles measured by the ISPM;

FIG. 4A is a horizontal cross sectional view of the ISPM, FIG. 4B is a front view of a linear anode PMT of a photodetector used in the ISMP, and FIG. 4C is a graph showing distribution of the number of particles measured by the ISPM;

FIG. 6A shows the NPPC particle in a main exhaust line, and FIG. 6B shows a signal wave corresponding to scattered light generated from the NPPC particle;

FIGS. 7A to 7C are explanatory diagrams of a detached particle or a backflow particle. FIG. 7A shows the detached particle in the main exhaust line, FIG. 7B shows the backflow particle in the main exhaust line, and FIG. 7C shows a signal wave corresponding to scattered light generated from the detached particle or the backflow particle.

DETAILED DESCRIPTION OF THE INVENTION

Hereinafter, the embodiments of the present disclosure will be described in detail with reference to the accompanying drawings.

First of all, a particle number measurement method in accordance with a first embodiment of the present disclosure will be described.

Figure 1:
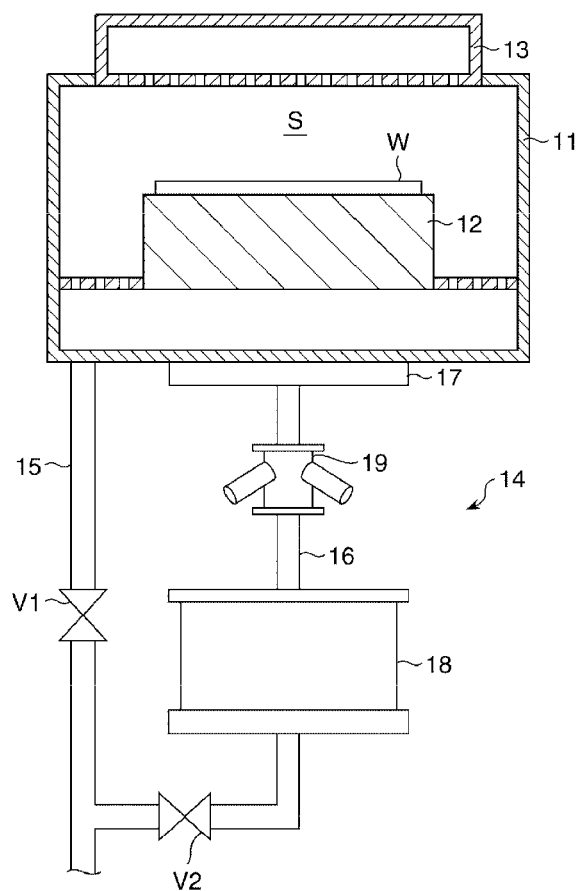
FIG. 1 is a cross sectional view schematically showing a configuration of a substrate processing apparatus to which a particle number measurement method in accordance with a first embodiment of the present disclosure is applied.

FIG. 1 is a cross sectional view schematically showing a configuration of a substrate processing apparatus to which the particle number measurement method in accordance with the embodiment of the present disclosure is applied. This substrate processing apparatus performs a plasma etching process on a wafer for a semiconductor device (hereinafter, simply referred to as a "wafer") as a substrate.

Referring to FIG. 1, a substrate processing apparatus 10 may include a processing chamber 11 for accommodating a wafer W. A cylindrical susceptor 12 is provided in the chamber 11, and a circular plate-shaped shower head 13 is disposed at an upper region within the chamber 11 so as to face the susceptor 12. Further, a gas exhaust system 14 for evacuating the inside of the chamber 11 is connected to the substrate processing apparatus 10.

The susceptor 12 has therein an electrostatic chuck, and the electrostatic chuck electrostatically attracts and holds the wafer W on the top surface of the susceptor 12 by a Coulomb force or the like. Moreover, a high frequency power supply (not shown) is connected to the susceptor 12 and serves as a lower electrode for applying a high frequency power to a processing space S between the susceptor 12 and the shower head 13. The shower head 13 is connected to a processing gas supply unit (not shown). Further, the shower head 13 diffuses and introduces a processing gas from the processing gas supply unit into the processing space S.

The gas exhaust system 14 may include a rough exhaust line 15, a main exhaust line 16 (exhaust pipe), and an APC valve 17. The rough exhaust line 15 is connected, at a downstream side thereof, to a dry pump (not shown) and roughly exhausts the inside of the chamber 11. The main exhaust line 16 may have a turbo molecular pump (hereinafter, referred to as a "TMP") 18, and the inside of the chamber 11 is evacuated to a high vacuum state by the TMP 18. Specifically, the dry pump depressurizes the chamber 11 from the atmospheric pressure to a medium vacuum state (e.g., about $1.3 \times 10$ Pa (0.1 Torr) or lower), and the TMP 18 cooperates with the dry pump to depressurize the chamber 11 to a high vacuum state of a pressure (e.g., about $1.3 \times 10^{-3}$ Pa ($1.0 \times 10^{-5}$ Torr) or lower) lower than that of the medium vacuum state.

The main exhaust line 16 is connected to the rough exhaust line 15 at a downstream side of the TMP 18. The rough exhaust line 15 and the main exhaust line 16 are provided with valves V1 and V2 capable of blocking the respective lines. The APC valve 17 such as a butterfly valve or a slide valve is installed between the chamber 11 and the TMP 18 and controls a pressure within the chamber 11 to a desired level.

In the substrate processing apparatus 10, after the inside of the chamber 11 is depressurized to the high vacuum state by evacuating the chamber 11 by the gas exhaust system 14, the processing gas is introduced into the processing space S from the shower head 13, and the high frequency power is applied to the processing space S by the susceptor 12. At this time, the processing gas is excited into plasma, and the wafer W is plasma-etched by positive ions or radicals in the plasma.

An operation of each component of the above-mentioned substrate processing apparatus 10 is controlled by a CPU of a control unit (not shown) of the substrate processing apparatus 10 based on a program corresponding to the plasma etching process.

In the substrate processing apparatus 10, the gas exhaust system 14 may include an ISPM (In Situ Particle Monitor) 19 provided on the main exhaust line 16. The ISPM 19 optically measures the number of particles flowing within the main exhaust line 16.

Figure 2A:
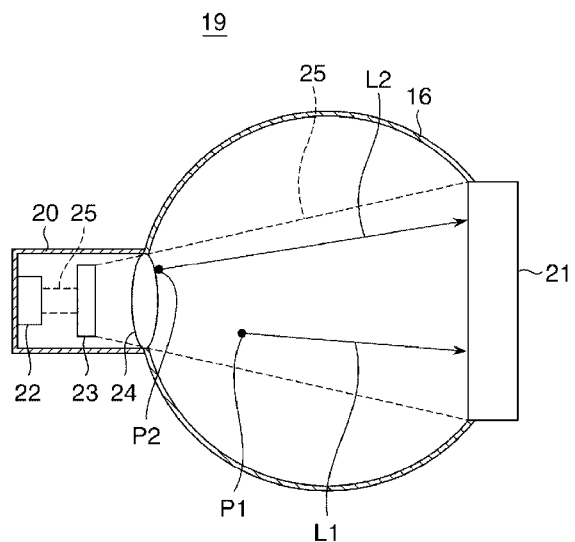
FIGS. 2A and 2B are explanatory diagrams of an ISPM of the substrate processing apparatus of FIG. 1.
Figure 2B:
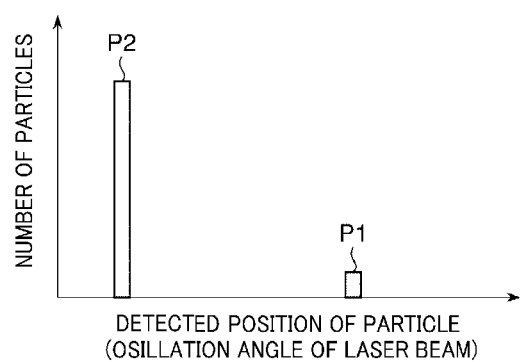

FIGS. 2A and 2B are explanatory diagrams of the ISPM of the substrate processing apparatus of FIG. 1. FIG. 2A is a horizontal cross sectional view of the ISPM, and FIG. 2B is a graph showing distribution of the number of particles measured by the ISPM.

Referring to FIG. 2A, the ISPM 19 may include a laser beam oscillator 20 for irradiating laser beam into the main exhaust line 16; and a photodetector 21 for receiving scattered light. The laser beam oscillator 20 may have a laser diode 22 for emitting laser beam 25; a laser beam scanning unit 23 for scanning a predetermined angle range within the main exhaust line 16 by the laser beam 25 by diffusing or refracting the emitted laser beam; and a glass window 24 for partitioning the laser diode 22 or the laser beam scanning unit 23 from the inside of the main exhaust line 16.

When the laser beam 25 irradiated from the laser beam oscillator 20 crosses with a particle P1 moving within the main exhaust line 16, scattered light L1 is generated from the particle P1. The intensity of the scattered light depends on the size of the particle P1, and the generation duration of the scattered light L1 depends on a time period during which the particle P1 passes through the laser beam 25, i.e., the moving speed of the particle P1.

A multiple number of photomultiplier tubes (hereinafter, referred to as "PMTs") are arranged in the photodetector 21, and each of the PMTs converts the intensity of the received scattered light to an electrical signal and transmits the electrical signal to the control unit of the substrate processing apparatus 10. In the electrical signal, the scattered light generated from the particle is represented in the form of a signal wave.

The control unit receives the electrical signal and calculates the distribution of the number of particles moving within the main exhaust line 16 based on the magnitude, the generation frequency, and the generation duration of the signal wave in the electrical signal or the position information of the PMT that has transmitted the electrical signal.

Here, a particle P2 may be attached to the glass window 24 as a contaminant. In this case, the laser beam 25 crosses with the particle P2 and scattered light L2 is generated from the particle P2. The scattered light L2 is received and converted to an electrical signal by the photodetector 21, and this electrical signal is transmitted to the control unit. Therefore, the particle P2 may be mistakenly detected as a particle moving within the main exhaust line 16.

When the oscillation of the laser beam 25 and the reception of the scattered light are repeated by the ISPM 19, the particle P1 moving within the main exhaust line 16 crosses with the laser beam 25 only once, whereas the particle P2 attached to the glass window 24 crosses with the laser beam 25 whenever the laser beam 25 is oscillated. Therefore, during a predetermined time period, the particle P1 generates scattered light only once, whereas the particle P2 generates scattered light several times.

Here, the control unit assumes that the generation frequency of the scattered light (the signal wave in the electrical signal) is proportional to the number of particles. Hence, it is assumed that a single particle P1 is detected at a laser beam oscillation angle (particle detection position) corresponding to the position of the particle P1, whereas several tens to several hundreds of particles P2 are detected at a laser beam oscillation angle corresponding to the position of the particle P2, as can be seen from FIG. 2B. Accordingly, when several tens to several hundreds of particles are detected at the same laser beam oscillation angle, the detected particle can be considered as a static particle P2 attached to the glass window 24 as a contaminant.

For this reason, in the particle number measurement method using the ISPM 19, scattered light having unusual generation frequency or unusual generation duration is excluded from the measurement. Specifically, among a multiple number of scattered lights received by the photodetector 21, scattered lights generated several tens to several hundreds times at the same laser beam oscillation angle are considered to be generated from a static particle attached to the glass window 24 as a contaminant, and, thus, are excluded from the measurement. That is, when the distribution of the number of particles is calculated, the number of static particles is subtracted from the measured number of particles within the main exhaust line 16.

The aforementioned ISPM 19 scans the inside of the main exhaust line 16 by the laser beam 25. However, it is also possible to use an ISPM that does not scan the inside of the main exhaust line 16 by the laser beam.

Figure 3A:
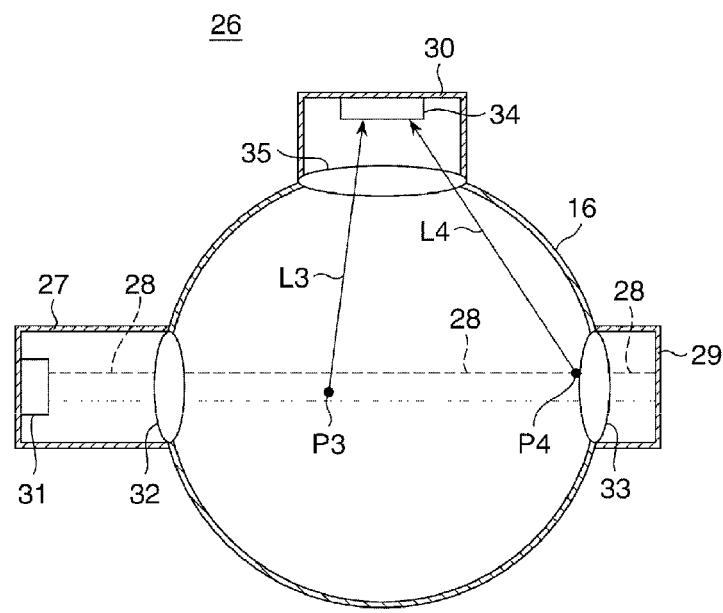
FIGS. 3A to 3C are explanatory diagrams of an ISPM in accordance with a first modification example.
Figure 3B:
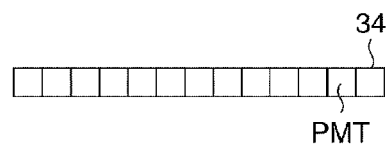
Figure 3C:
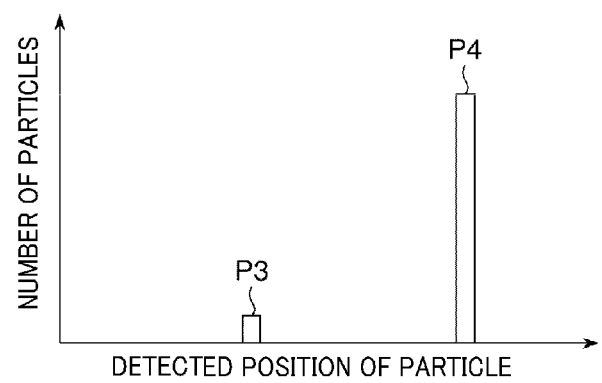

FIGS. 3A to 3C are explanatory diagrams of an ISPM in accordance with a first modification example. FIG. 3A is a horizontal cross sectional view of the ISPM, FIG. 3B is a front view of a linear anode PMT of a photodetector used in the ISPM, and FIG. 3C is a graph showing distribution of the number of particles measured by the ISPM.

Referring to FIG. 3A, the ISPM 26 may include a laser beam oscillator 27 for irradiating laser beam 28 into the main exhaust line 16; a laser beam absorber 29 for receiving the irradiated laser beam 28; and a photodetector 30 for receiving scattered light. The laser beam oscillator 27 may have a laser diode 31 for emitting the laser beam 28, and a glass window 32 for partitioning the laser diode 31 from the inside of the main exhaust line 16. The laser beam absorber 29 may have a reflection preventing unit (not shown) for absorbing the irradiated laser beam 28 or reflecting the irradiated laser beam 28 in a direction different from the irradiation direction; and a glass window 33 for partitioning the reflection preventing unit from the inside of the main exhaust line 16. Further, the photodetector 30 may have a linear anode PMT 34 (see FIG. 3B) formed by arranging a multiple number of PMTs in one dimension, and a glass window 35 for partitioning the linear anode PMT 34 from the inside of the main exhaust line 16.

When the laser beam 28 irradiated from the laser beam oscillator 27 crosses with a particle P3 moving within the main exhaust line 16, scattered light L3 is generated from the particle P3. A PMT corresponding to the position of the particle P3 in the linear anode PMT 34 receives the scattered light L3 and converts the intensity of the received scattered light L3 to an electrical signal. This electrical signal is transmitted to the control unit of the substrate processing apparatus 10.

Here, a particle P4 may be attached to the glass window 32 or 33 as a contaminant (FIG. 3A shows a state in which the particle P4 is attached to the glass window 33). In this case, the laser beam 28 crosses with the particle P4, and scattered light L4 is generated from the particle P4. The scattered light L4 is received and converted to an electrical signal by the photodetector 30, and this electrical signal is transmitted to the control unit. Therefore, when the oscillation of the laser beam 28 and the reception of the scattered light are repeated by the ISPM 26, it is assumed that several tens to several hundreds of particles are detected by the PMT corresponding to the position of the particle P4 (particle detection position) as shown in FIG. 3C.

That is, in the case of using the ISPM 26 as well as in the case of using the ISPM 19, when several tens to several hundreds of particles are detected by a certain PMT, the detected particles are considered as a static particle P4 attached to the glass window 33 as a contaminant.

For that reason, in the particle number measurement method using the ISPM 26, when the scattered lights generated several tens to several hundreds times are received by a certain PMT, the scattered lights are considered to be generated from a static particle attached to the glass window 32 or 33 and thus are excluded from the measurement.

Figure 4A:
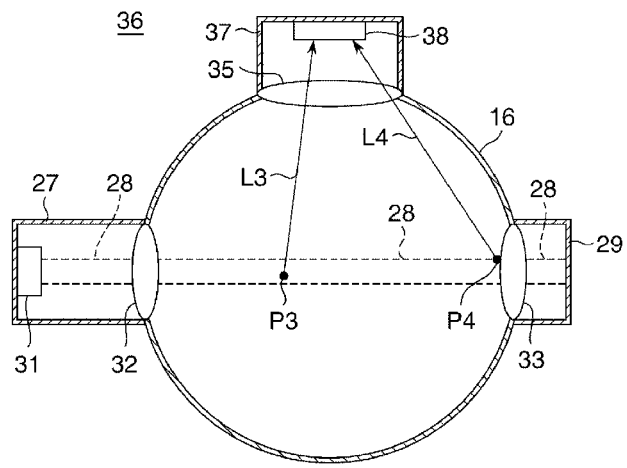
FIGS. 4A to 4C are explanatory diagrams of an ISPM in accordance with a second modification example.
Figure 4B:
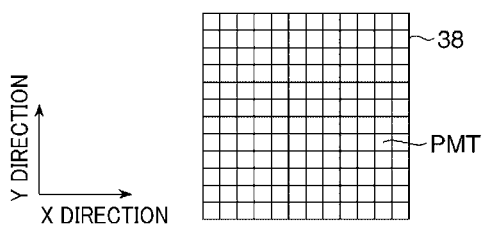
Figure 4C:
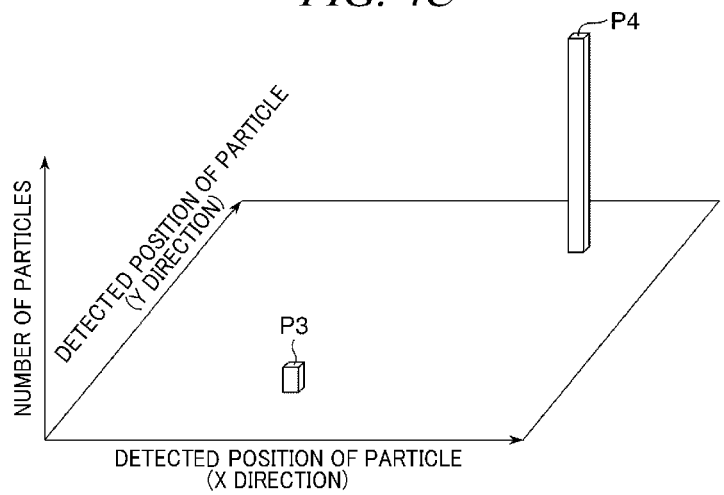

FIGS. 4A to 4C are explanatory diagrams of an ISPM in accordance with a second modification example. FIG. 4A is a horizontal cross sectional view of the ISPM, FIG. 4B is a front view of a linear anode PMT of a photodetector used in the ISPM, and FIG. 4C is a graph showing distribution of the number of particles measured by the ISPM. The ISPM 36 in accordance with the second modification example has the same configuration and operation as those of the above-described ISPM 26. Hence, redundant explanation of the same configuration and operation may be omitted, and the different configuration and operation will be discussed hereinafter.

Referring to FIG. 4A, the ISPM 36 may include a laser beam oscillator 27, a laser beam absorber 29, and a photodetector 37 for receiving scattered light. The photodetector 37 may have a multi anode PMT 38 (see FIG. 4B) formed by arranging a multiple number of PMTs two-dimensionally; and a glass window 35 for partitioning the multi anode PMT 38 from the inside of the main exhaust line 16. In the photodetector 37, a CCD, a CCD having an image intensifier or a CMOS image sensor can be used instead of the multi anode PMT.

In the ISPM 36, when the oscillation of the laser beam 28 and the reception of the scattered light are repeated, several tens to several hundreds of particles are detected by the PMT corresponding to the position of the particle P4 (particle detection position) attached to the glass window 33 as a contaminant, as shown in FIG. 4.

That is, in the case of using the ISPM 36, when several tens to several hundreds of particles are detected by a certain PMT, the detected particles are considered as a static particle P4 attached to the glass window 33 as a contaminant.

Accordingly, in the particle number measurement method using the ISPM 36, when the scattered lights generated several tens to several hundreds times are received by a certain PMT, the scattered lights are considered to be generated from a static particle attached to the glass window 32 or 33 and thus is excluded from the measurement.

In the particle number measurement method in accordance with the present embodiment shown in FIGS. 2 to 4, the static particles are considered as the particles P2 (P4) attached to the glass window 24 (32 or 33) as a contaminant, and the number of the static particles is subtracted from the number of particles measured within the main exhaust line 16. Hence, the number of particles moving within the main exhaust line 16 can be accurately measured by subtracting the number of particles attached to the glass window 24, 32 or 33 as a contaminant.

Further, in the particle number measurement method in accordance with the present embodiment, the number of particles moving within the main exhaust line 16 can be accurately measured even when the contaminants are attached to the glass window 24, 32 or 33. Therefore, the glass window 24, 32 or 33 need not be cleaned frequently. As a consequence, the frequency of a maintenance operation can be reduced, and the operation rate of the substrate processing apparatus 10 can be improved. Besides, a degree of cleanness of the glass window 24, 32 or 33 need not be high, so that a time required for the maintenance operation can be decreased.

In the above-described particle number measurement method in accordance with the present embodiment, the number of particles moving within the main exhaust line 16 can be measured. However, this particle number measurement method can also be used for measuring the number of particles moving within the chamber 11 by using an ISPM installed at the chamber 11.

Moreover, in the above-described particle number measurement method in accordance with the present embodiment, the particles attached to the glass window 24, 32 or 33 as a contaminant may be detected. When the particles attached to the glass window 24, 32 or 33 as a contaminant are detected, an alarm indicating the detection of contaminants may be displayed on a display (not shown) of the substrate processing apparatus 10. Further, the positions of the particles attached to the glass window 24, 32 or 33 may be specified by specifying a PMT that has detected the particles attached to the glass window 24, 32 or 33. Hence, the specified attaching positions may be displayed on the display together with the alarm.

Hereinafter, the particle number measurement method in accordance with a second embodiment of the present disclosure will be described.

This embodiment has the same configuration and operation as those of the first embodiment except in that the type of particles to be excluded from the measurement is different. Therefore, redundant explanation of the same configuration and operation may be omitted, and the different configuration and operation will be described hereinafter.

Recently, as for a method for removing particles from the inside of a chamber of a substrate processing apparatus, an NPPC (Non Plasma Particle Cleaning) sequence (particle removing process) which does not use plasma is employed (see, e.g., Japanese Patent Laid-open Publication No. 2005-317900). In the NPPC sequence, particles are detached from the components within the chamber by a gas impact force, a gas viscous force and an electromagnetic stress and then discharged from the chamber.

Figure 5:
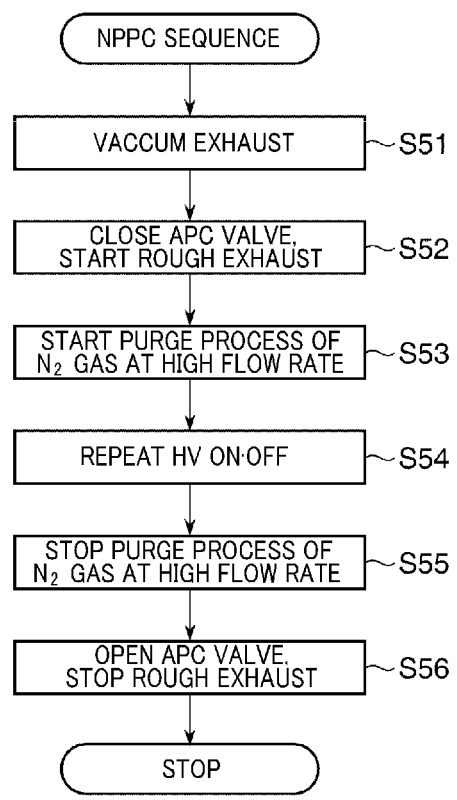
FIG. 5 is a flowchart of an NPPC sequence.

FIG. 5 is a flowchart of the NPPC sequence. The NPPC sequence is performed in a state where the wafer W is not accommodated within the chamber 11.

Referring to FIG. 5, the APC valve 17 is opened, and the inside of the chamber 11 is evacuated to a vacuum state by the TMP 18 or the dry pump (step S51). When the pressure in the chamber 11 is reduced to a predetermined level, the APC valve 17 is closed and the inside of the chamber 11 is roughly evacuated by the dry pump (step S52).

Thereafter, a $N_2$ gas as a purge gas is introduced into the chamber 11 from the shower head 13 at a high flow rate (step S53). At this time, a gas impact wave is generated within the chamber 11. When the gas impact wave reaches the surfaces of the components within the chamber 11, the gas impact force caused by the gas impact wave affects the particles attached to the surfaces of the components. Accordingly, the particles are detached from the surfaces of the components and discharged through the gas exhaust system 14. Moreover, the $N_2$ gas as a purge gas is still supplied into the chamber 11, so that the viscous flow of $N_2$ gas is generated within the chamber 11. When the viscous flow reaches the surfaces of the components, the gas viscous force caused by the viscous flow affects the particles attached to the surfaces of the components. As a consequence, the particles are detached from the surfaces of the components and discharged through the gas exhaust system 14.

If the pressure within the chamber 11 is higher than a predetermined pressure, the viscous flow is easily generated. Therefore, the APC valve 17 controls the pressure within the chamber 11 to be maintained at a predetermined pressure, e.g., about 133 Pa (1 Torr) or higher, and desirably about several ten-thousands Pa (several hundreds Torr) or higher.

Here, the gas introduced into the chamber 11 is not limited to a $N_2$ gas, and may be an $O_2$ gas or an inert gas such as helium (He), neon (Ne), argon (Ar), krypton (Kr), xenon (Xe), radon (Rn) or the like.

Thereafter, the application and the non-application of a DC high voltage HV from a non-illustrated DC power supply to the electrostatic chuck of the susceptor 12 are repeated (step S54). At this time, an electrostatic field is generated by the application of the high voltage to the electrostatic chuck, and the electromagnetic stress acts on the surfaces of the components within the chamber 11. Accordingly, the particles are detached from the surfaces of the components and discharged through the gas exhaust system 14.

The electromagnetic stress effectively acts on the surfaces of the components when the application of the high voltage to the electrostatic chuck is started or stopped. Here, the high voltage is repetitively applied to the electrostatic chuck in the substrate processing apparatus 10, so that the electromagnetic stress repetitively acts on the surfaces of the components. As a consequence, the particles attached to the surfaces of the components can be removed.

Then, the operation of supplying the $N_2$ gas as a purge gas from the shower head 13 at a high flow rate is stopped (step S55). Thereafter, the APC valve 17 is opened, and the rough exhaust operation using the dry pump is stopped (step S56). In this manner, the NPPC sequence is completed.

Generally, it is assumed that the number of particles within the chamber and the number of particles flowing in the gas exhaust system 14 are related. Hence, in order to estimate the number of particles within the chamber during the execution of the NPPC sequence, the number of particles (hereinafter, referred to as "NPPC particles") generated within the main exhaust line 16 by the NPPC sequence (specific factor) is measured.

Meanwhile, the APC valve 17 is opened or closed in the initial or the final step of the NPPC sequence. Therefore, the particles may be detached from the APC valve 17 by the impact of the opening and closing operation and the detached particles (hereinafter, referred to as "detached particles") may exist within the main exhaust line disposed at the downstream side of the APC valve 17. Further, during the entire NPPC sequence, the particles are sucked into the TMP 18 via the main exhaust line 16. The sucked particles may collide with a rotary wing rotating at a high speed within the TMP 18 and return into the main exhaust line 16 by high kinetic energy generated by the collision.

Thus, even though the ISPM is installed within the main exhaust line 16 to measure the number of particles flowing in the main exhaust line 16, the backflow particles as well as the NPPC particles may be detected during the execution of the NPPC sequence. Especially, in the initial step of the NPPC sequence, the backflow particles may be detected in addition to the detached particles.

However, in the NPPC sequence, a large amount of particles are detached from the components within the chamber 11 and introduced into the gas exhaust system 14 for a few seconds after the beginning of the NPPC sequence. Thus, in order to estimate the number of particles within the chamber, the number of particles generated in the initial step of the NPPC sequence needs to be accurately measured. That is, it is required to accurately categorize the particles moving within the main exhaust line 16 during the initial step of the NPPC sequence into the NPPC particles, the detached particles and the backflow particles.

Here, during the execution of the NPPC sequence, a high-speed gas flow is created from the inside of the chamber 11 into the main exhaust line 16 by the process of supplying the $N_2$ gas at a high flow rate, and the NPPC particles move from the inside of the chamber 11 into the main exhaust line 16 by the high-speed gas flow. Accordingly, the NPPC particles uniformly move at a high speed toward the downstream side of the main exhaust line 16. Meanwhile, the detached particles do not move from the inside of the chamber 11 into the main exhaust line 16. Hence, the detached particles are not affected by a high-speed gas flow and thus move at a low speed. In addition, the backflow particles move toward the upstream side of the main exhaust line 16 within the main exhaust line 16 and the backflow particles move at a low speed due to the resistance of a gas exhaust flow within the main exhaust line 16.

Figure 6A:
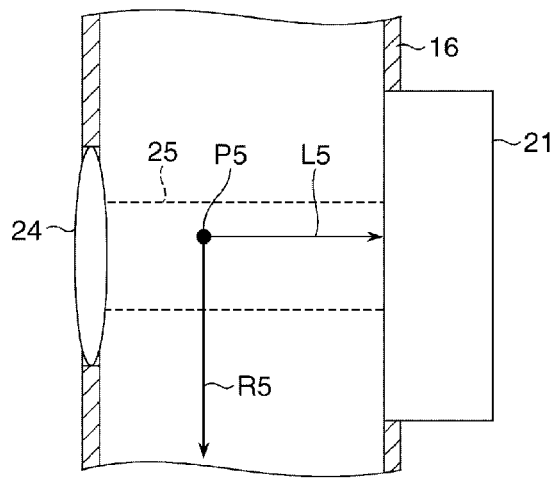
FIGS. 6A and 6B are explanatory diagrams of an NPPC particle.
Figure 6B:
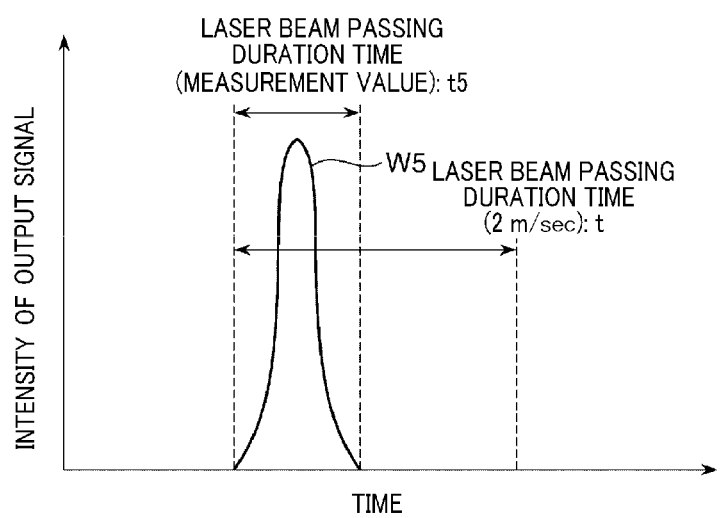

FIGS. 6A and 6B are explanatory diagrams of the NPPC particle. FIG. 6A shows the NPPC particle within the main exhaust line, and FIG. 6B shows a signal wave corresponding to scattered light generated from the NPPC particle. Although the ISPM 19 is used in the main exhaust line 16, only a part of the ISPM 19 (the glass window 24, the laser beam 25 and the photodetector 21) is illustrated in FIG. 6A for the convenience of explanation.

As shown in FIG. 6A, within the main exhaust line 16, the NPPC particle P5 moves toward the downstream side (the lower side in the drawing) of the main exhaust line 16 along a path R5 by the high-speed gas flow. While the NPPC particle P5 is passing through the laser beam 25, scattered light L5 is continuously generated from the NPPC particle P5. Since, however, the NPPC particle P5 moves at a high speed, the generation duration of the scattered light L5 is short. Hence, as shown in FIG. 6B, a signal wave W5 converted from the scattered light L5 received by the photodetector 21 has a short wavelength.

Here, the wavelength of the signal wave W5 is proportional to a time period t5 during which the NPPC particle P5 passes through the laser beam 25. The present inventor has found that the time period t5 is generally shorter than a time period t during which a particle having a moving speed of about 2 m/sec passes through the laser beam 25.

Meanwhile, as shown in FIG. 7A, within the main exhaust line 16, the detached particle P6 moves toward the downstream side (downward direction of the drawing) of the main exhaust line 16 along a path R6 by gravity or the like. Further, as shown in FIG. 7B, within the main exhaust line 16, the backflow particle P7 moves toward the upstream side (upward direction of the drawing) of the main exhaust line 16 along a path R7. When the detached particle P6 or the backflow particle P7 passes through the laser beam 25, the scattered light L6 or L7 is continuously generated from the detached particle P6 or the backflow particle P7. Since, however, the detached particle P6 or the backflow particle P7 moves at a low speed, the generation duration of the scattered lights L6 and L7 is long. Therefore, as shown in FIG. 7C, the signal wave W6 converted from the scattered light L6 or L7 received by the photodetector 21 has a long wavelength.

Here, the wavelength of the signal wave W6 is proportional to a time period t6 required for the detached particles P6 or the backflow particles P7 to pass through the laser beam 25. The present inventor has found that the time period t6 is generally longer than a time period t required for a particle having a moving speed of about 2 m/sec to pass through the laser beam 25.

Hence, in the particle number measurement method in accordance with the present embodiment, the NPPC particle P5 is distinguished from the detached particle P6 or the backflow particle P7 based on the moving speed. Specifically, a particle having a moving speed higher than about 2 m/sec is determined to be the NPPC particle P5, whereas a particle having a moving speed lower than about 2 m/sec is determined to be the detached particle P6 or the backflow particle P7. That is, when the number of particles moving within the main exhaust line 16 is measured, the particle having a moving speed lower than about 2 m/sec is not counted.

In the particle number measurement method in accordance with the present embodiment, a particle having a moving speed lower than about 2 m/sec is determined to be the detached particle P6 or the backflow particle P7, and the number of particles having a moving speed lower than about 2 m/sec is subtracted from the number of particles measured within the main exhaust line 16. Accordingly, the number of the NPPC particles P5 within the main exhaust line 16 can be accurately measured by excluding the number of the detached particles P6 or the backflow particles P7 from the measurement.

Since the backflow particle P7 moves within the main exhaust line 16 toward the upstream side thereof against the gas exhaust flow, the particles moving within the main exhaust line 16 against the gas exhaust flow can be excluded from the measurement regardless of the moving speed of the particles. Accordingly, the number of the backflow particles P7 can be accurately excluded from the measurement.

Figure 8:
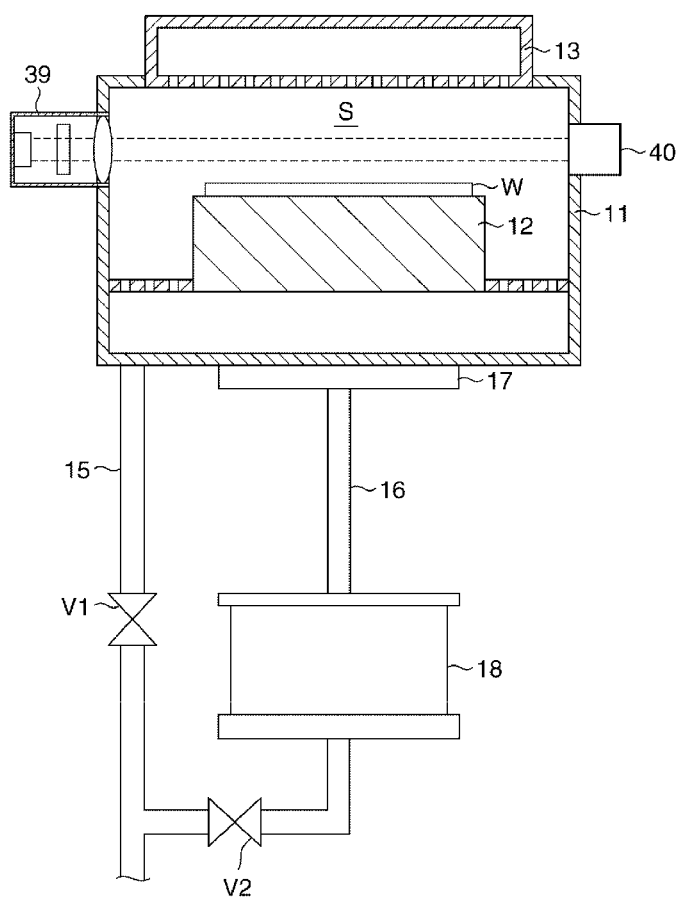
FIG. 8 is explanatory diagram for describing the case of measuring the number of particles moving within a chamber by an ISPM installed at the chamber.

In the particle number measurement method in accordance with the above-described embodiment, the number of particles moving within the main exhaust line 16 is measured. However, this particle number measurement method can be used to measure the number of particles moving within the chamber 11 by installing the ISPM including the laser beam oscillator 39 and the photodetector 40 at the chamber as shown in FIG. 8. Here, the present inventor has found that the NPPC particle P5 within the chamber 11 is moved by the high-speed gas flow for a short time period and has a low moving speed compared to that of the NPPC particle P5 within the gas exhaust line 16, and thus the NPPC particle P5 moves at a minimum speed of about 1 m/sec. Meanwhile, the present inventor has found that the detached particle P6 or the backflow particle P7 enters the chamber 11 against the gas exhaust flow within the main exhaust line 16 and moves at an extremely low speed, and thus the detached particle P6 or the backflow particle P7 moves at a maximum of about 1 m/sec.

Therefore, the number of particles having a moving speed of lower than about 1 m/sec during the execution of the NPPC sequence is subtracted from the number of particles measured within the chamber 11. As a consequence, the number of NPPC particles P5 in the chamber 11 can be accurately measured.

Moreover, in the particle number measurement method in accordance with the present embodiment, the inside of the chamber 11 is exhausted to a vacuum state. However, even when the pressure within the chamber 11 is an atmospheric pressure, the particle number measurement method in accordance with the present embodiment can be used by properly setting a maximum moving speed of particles to be excluded from the measurement.

In the aforementioned embodiments, a substrate on which a plasma etching process is performed is not limited to a wafer for a semiconductor device, and may be various substrates used for a FPD (Flat Panel Display) including a LCD (Liquid Crystal Display), or a photomask, a CD substrate, or a print substrate.

The present disclosure can be implemented by providing a storage medium which stores a software program implementing the function of each embodiment to a computer and by reading and executing the program stored in the storage medium by a CPU of the computer.

In this case, the program read out from the storage medium implements the functions of the aforementioned embodiments, and, thus, the program and the storage medium storing the program constitute the present disclosure.

Moreover, by way of example, as a storage medium for providing the program, a RAM, an NV-RAM, a floppy (registered trademark) disk, a hard disk, a magneto-optical disk, an optical disk such as a CD-ROM, a CD-R, a CD-RW, a DVD (a DVD-ROM, a DVD-RAM, a DVD-RW, a DVD+RW), a magnetic tape, a non-volatile memory card, or another ROM can be used. Alternatively, the program may be supplied to the computer by downloading it from another computer (not shown) or database connected to Internet, a commercial network, a local area network or the like.

The function of each embodiment can be implemented by executing the program read by the CPU of the computer, and an OS (operating system) operated on the CPU may perform a part or all of the actual process in response to instructions of the program and the function of each embodiment may be implemented by the process.

Further, the program read from the storage medium may be written in a memory of a function extension board inserted into the computer or a function extension unit connected to the computer, and a CPU of the function extension board or the function extension unit may perform a part or all of the actual process in response to instructions of the program and the function of each embodiment may be implemented by the process.

The program may include an object code, a program executable by an interpreter, script data provided to an OS, or the like.

What is claimed is:

1. A particle number measurement method comprising:
    irradiating laser beam into a predetermined space via a window, receiving light scattered from a particle crossing with the laser beam, and calculating the number of first particles based on the received scattered light; and
    measuring the number of particles generated by a specific factor and moving within the predetermined space by subtracting the number of second particles that are static from the calculated number of the first particles, the second particles being defined as contaminants attached to the window.

2. The particle number measurement method of claim 1, wherein the specific factor includes a process of removing particles within a processing chamber of a substrate processing apparatus by purging the processing chamber by a gas at a high flow rate.

3. The particle number measurement method of claim 2, wherein the predetermined space is the inside of the processing chamber,
    the inside of the processing chamber is exhausted to a vacuum state, and
    the predetermined moving speed is about 1 m/sec.

4. The particle number measurement method of claim 2, wherein the predetermined space is the inside of a gas exhaust line for exhausting gas from the inside of the processing chamber,
    the inside of the processing chamber is exhausted to a vacuum state, and
    the predetermined moving speed is about 2 m/sec.

5. The particle number measurement method of claim 1, wherein the predetermined space is the inside of a gas exhaust line for exhausting gas from the inside of the processing chamber,
    the inside of the processing chamber is exhausted to a vacuum state, and
    the number of third particles moving in a predetermined moving direction opposite to a direction in which the gas flows in the gas exhaust line is further subtracted from the calculated number of first particles.

* * * * *

UNITED STATES PATENT AND TRADEMARK OFFICE
CERTIFICATE OF CORRECTION

PATENT NO. : 8,531,664 B2  
APPLICATION NO. : 13/036152  
DATED : September 10, 2013  
INVENTOR(S) : Hiroshi Nagaike Page 1 of 1

It is certified that error appears in the above-identified patent and that said Letters Patent is hereby corrected as shown below:

In the specification, Column 10, line 51, add --16-- after "line"

Signed and Sealed this
Twelfth Day of November, 2013

Teresa Stanek Rea
*Deputy Director of the United States Patent and Trademark Office*